United States Patent
Reman et al.

[11] Patent Number: 5,488,184
[45] Date of Patent: Jan. 30, 1996

[54] PROCESS FOR THE PREPARATION OF ALKYLENE GLYCOLS

[75] Inventors: Willem G. Reman; Eugene M. G. A. Van Kruchten, both of Amsterdam, Netherlands

[73] Assignee: Shell Oil Company, Houston, Tex.

[21] Appl. No.: 381,452

[22] Filed: Jan. 31, 1995

[30] Foreign Application Priority Data

Jan. 31, 1994 [EP] European Pat. Off. ............ 94200255

[51] Int. Cl.$^6$ .......................... C07C 29/00; C07C 31/20; C07C 31/22
[52] U.S. Cl. .......................................... 568/867
[58] Field of Search .............................. 568/867

[56] References Cited

U.S. PATENT DOCUMENTS

| | | | |
|---|---|---|---|
| 4,393,254 | 7/1983 | Johnson et al. | 568/867 |
| 4,967,018 | 10/1990 | Soo et al. | 568/867 |
| 4,982,021 | 1/1991 | Best et al. | 568/867 |

FOREIGN PATENT DOCUMENTS

| | | | |
|---|---|---|---|
| 0156449 | 10/1985 | European Pat. Off. | |
| 0226799 | 7/1987 | European Pat. Off. | |
| 57-139026 | 8/1982 | Japan. | |
| 2002726 | 10/1995 | U.S.S.R. | 568/867 |
| 2001901 | 10/1995 | U.S.S.R. | 568/867 |

*Primary Examiner*—Joseph E. Evans

[57] ABSTRACT

A process for the preparation of alkylene glycols comprising reacting an alkylene oxide with water in the presence of a catalyst composition comprising a solid material having one or more electropositive sites, which are coordinated with one or more anions other than metalate or halogen anions, with the proviso that when the solid material is an anionic exchange resin of the quaternary ammonium type and the anion is bicarbonate, the process is performed in the substantial absence of carbon dioxide.

10 Claims, No Drawings

PROCESS FOR THE PREPARATION OF ALKYLENE GLYCOLS

FIELD OF THE INVENTION

The invention relates to a process for the preparation of alkylene glycols by reaction of an alkylene oxide with water in the presence of a catalyst.

BACKGROUND OF THE INVENTION

Alkylene glycols, in particular monoalkylene glycols, are of established commercial interest. For example, monoalkylene glycols are being used in anti-freeze compositions, as solvents and as base materials in the production of polyethylene terephthalates e.g. for fibers or bottles.

The production of alkylene glycols by hydrolysis of alkylene oxides is known, both by liquid phase hydration of alkylene oxides with an excess amount of water, e.g. of 20 to 25 moles of water per mole of alkylene oxide, or by hydration in a heterogeneous system. The reaction is deemed to be a nucleophilic substitution reaction, whereby opening of the alkylene oxide ring occurs, water acting as the nucleophile. Because the primarily formed monoalkylene glycol likewise acts as nucleophile, as a rule a mixture of monoalkylene glycol, dialkylene glycol and higher alkylene glycols is formed. In order to increase the selectivity to monoalkylene glycols, it is necessary to suppress the reaction between the primary product and alkylene oxide, which competes with the hydrolysis of alkylene oxide.

One effective means for suppressing the secondary reaction is to increase the relative amount of water present in the reaction mixture. Although the selectivity with respect to the monoalkylene glycol is thus improved, a problem consists in that for the recovery of the monoalkylene glycol from the reaction mixture, large amounts of water have to be removed. This is usually done by evaporation, which is followed by distillation of the desired product from the evaporation residue. It will be understood that the separation of large amounts of water from the product involves large expenditure and is economically unattractive.

Considerable efforts have been made in order to achieve an increase in selectivity with respect to the monoalkylene glycols, without having to use a large excess of water. Usually, these efforts have focused on the selection of more active hydration catalysts and in fact there are many publications, in which results obtained with various types of catalysts are disclosed.

Both acid and alkaline hydration catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

In U.S. Pat. No. 4,393,254, a process for the hydration of alkylene oxides is described whereby use is made of partially amine-neutralized sulfonic acid resins as catalysts, for example Amberlyst XN-1010, neutralized for 50% with triethylamine. Although these catalysts allow low water/alkylene oxide ratios, the obtainable conversions are unsatisfactory, typically about 70%.

Higher conversions can be obtained with the process, as disclosed in EP 156,449. According to this document, the hydrolysis of alkylene oxides is carried out in the presence of a selectivity-enhancing metalate anion-containing material, preferably a solid having electropositive complexing sites having affinity for the metalate anions. The said solid is preferably an anion exchange resin, the metalate anions are specified as molybdate, tungstate, metavanadate, hydrogenpyrovanadate and pyrovanadate anions. It is considered that an adduct is formed between the metalate anion and the alkylene oxide, which adduct is subsequently hydrolyzed to form the alkylene glycol. The formation of the adduct competes with the reaction between monoalkylene glycol and alkylene oxide which would result in the formation of di- and trialkylene glycols. The selectivity with respect to monoalkylene glycols is thus enhanced, without having to supply excessive amounts of water. However, a complication of this known process consists in that the alkylene glycol-containing product stream also comprises a substantial amount of metalate anions, displaced from the electropositive complexing sites of the solid metalate anion-containing material. In order to reduce the amount of metalate anions in the alkylene glycol product stream, this stream is contacted with a solid having electropositive complexing sites associated with anions which are replaceable by the said metalate anions.

It has been proposed to simplify the product recovery procedure by using water-insoluble vanadate and molybdate salts. However, with these metalate anion salts the obtained selectivities are significantly lower than with the water-soluble metalates.

EP-A-226,799 discloses a method for preparing ethylene glycol and/or propylene by hydrating the respective alkylene oxide in the presence of a catalytic combination of a carboxylic acid and a salt of a carboxylic acid, both of which may be used in an arbitrary combination. These acid/salt combinations are in solution, which makes their separation from the reaction product necessary.

JP-A-57-139026 discloses a method for reacting alkylene oxide with water in the presence of a halogen type anion exchange resin and in the co-presence of carbon dioxide.

RU-C-2001901 points out that the former disclosure has the disadvantage of the formation of carbonates in the reaction mixture, which are difficult to separate from the glycols on account of the closeness of their boiling points. This patent publication discloses as its invention the performance of the alkylene oxide hydrating reaction in one or in a sequence of 'extrusion reactor(s)' (continuous reaction), in the presence of 'anionite' (anion exchange resin of the quaternary ammonium type) in bicarbonate form and carbon dioxide. The essential difference with the former Japanese patent publication appears to be the use of the bicarbonate from of the anion exchanger instead of the halogen form thereof. And yet, the Russian patent does not dispense with the addition of carbon dioxide to the feed.

It has now been found that the preparation of alkylene glycols proceeds with high conversions and selectivities to the monoalkylene glycols, by performing the reaction with the aid of a specific catalyst composition, substantially free of metalate or halogen anions.

SUMMARY OF THE INVENTION

The invention therefore relates to a process for the preparation of alkylene glycols which comprises reacting an alkylene oxide with water in the presence of a catalyst composition comprising a solid material having one or more electropositive sites, which are coordinated with one or more anions other than metalate or halogen anions, with the proviso that when the solid material is an anionic exchange resin of the quaternary ammonium type and the anion is bicarbonate, the process is performed in the substantial absence of carbon dioxide.

DESCRIPTION OF THE PREFERRED EMBODIMENTS

The alkylene oxides, used as starting material in the process of the invention, have their conventional meaning, i.e. compounds having a vicinal oxide (epoxy) group in their molecules.

In particular suitable are alkylene oxides of the general formula

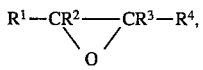

wherein $R^1$ to $R^4$ independently represent a hydrogen atom or a substituted or unsubstituted alkyl group having from 1 to 6 carbon atoms. Any alkyl group, represented by $R^1$, $R^2$, $R^3$ and/or $R^4$, preferably has from 1 to 3 carbon atoms. As substituents, inactive moieties, such as hydroxy groups may be present. Preferably, R1, $R^2$, and $R_3$ represent hydrogen atoms and $R^4$ represents a non-substituted $C_1$–$C_3$-alkyl group and, more preferably, $R^1$, $R^2$, $R^3$ and $R^4$ all represent hydrogen atoms.

Examples of suitable alkylene oxides therefore include ethyleneoxide, propyleneoxide, 1,2-epoxybutane, 2,3-epoxybutane and glycidol. Ethylene oxide and propylene oxide are of particular commercial importance.

As has been explained above, it is advantageous to perform the hydrolysis of the alkylene oxides, without using excessive amounts of water. In practice, amounts of water in the range of 1 to 15 moles per mole of alkylene oxide are quite suitable, amounts in the range of 1 to 6 on the same basis being preferred. In the process of the invention high selectivities with respect to the monoalkylene glycol are often already achieved, when only 4 or 5 moles of water per mole of alkylene oxide are supplied.

Suitable solid materials having one or more electropositive sites include inorganic materials such as silicas, silica-aluminas, clays and zeolites, and organic materials such as ion-exchange resins, in particular anion exchange resins.

Attractive results have been achieved with solid material containing tertiary amine or quaternary ammonium groups. These groups are connected with the matrix of the solid material and, under the reaction conditions, provide electropositive sites.

Suitable tertiary amine groups are, in particular, lower alkylamines, linked to the matrix of the solid material via a benzyl group.

Quaternary ammonium groups are preferred, in particular a trimethylbenzyl ammonium group.

Anionic exchange resins suitable for use in the present process are known per se. Many of these are commercially available and may be advantageously used in the process of the invention. Suitable examples of commercially available materials are Lewatit M 500 WS (Lewatit is a trade mark), Dualite A 368 (Dualite is a trade mark) and Amberlite IRA 400, (all based on polystyrene resins, cross-linked with divinylbenzene) and Reillex 425 (based on a polyvinylpyridine resin, cross-linked with divinylbenzene).

Although not wishing to rely on or to be bound by a specific reaction mechanism, it is considered possible that the coordination between the solid material and the coordinating compound will lead to the presence of a coordinated nucleophilic group, reacting with the alkylene oxide forming a readily hydrolyzable complex. While nothing is known about the extent of coordination during the reaction at an electropositive site of the solid material, it is probable that any such coordination is related to the nature of the coordinating compound and/or the group constituting the electropositive site.

Suitable coordinating compounds for use in the process of the invention are derived from neutral or weakly acidic compounds and include inorganic non-metalate and non-halogen anions such as bicarbonate, bisulfite, and phosphate, and organic anions such as carboxylates having 1 to about 20 carbon atoms, particularly formate, acetate, and propionate. The preferred anions are bicarbonate, bisulfite and formate. More than one coordinating compound can be used on a given solid material.

The catalyst composition according to the invention can be prepared by adding an aqueous solution of the coordinating compound to the solid material, which may or may not be adapted in a foregoing preparatory step. For example, when the solid material is a quaternary ammonium containing anion exchange resin and the coordinating anion is bicarbonate, the catalyst composition may be prepared in a single step by adding to the resin an aqueous solution of an alkali metal bicarbonate such as sodium bicarbonate, followed by washing with water, or alternatively, the catalyst composition can be prepared in two steps by first converting the resin to the hydroxyl form with a hydroxide such as aqueous sodium hydroxide, and subsequently adding carbon dioxide gas, followed by washing with water.

It is also possible in principle to perform the process in the presence of a catalyst composition which is formed in situ. For example, the process may be carried out in the presence of the solid material and of bicarbonate moieties formed in situ by adding carbon dioxide to the reaction mixture. For example, when the solid material is a tertiary amine and/or the coordinating compound is bisulfite, the addition of carbon dioxide to the reaction mixture was found to be advantageous. However, when the solid material is a quaternary ammonium-containing anion exchange resin and the coordinating compound is bicarbonate or formate, it was found that the process according to the invention should preferably be performed in the absence of any substantial amounts, i.e., less than about 0.1 wt % and preferably less than about 0.01 wt %, of carbon dioxide in the reaction mixture.

The process of the invention may be carried out in batch operation. However, in particular for large scale embodiments it is preferred to operate the process continuously.

In order to obtain adequate time-yield values, it is recommended to perform the process under elevated temperature and pressure conditions.

Suitable reaction temperatures are generally in the range from about 80° C. to about 200° C., whereby temperatures in the range from about 90° C. to about 150° C. are preferred. The reaction pressure is usually selected in the range of about 200 to about 3000 kPa, preferably in the range of about 200 to about 2000 kPa. For batch operations of the process, the selected reaction pressure is advantageously obtained by supplying carbon dioxide, or by pressurizing with an inert gas, such as nitrogen. If-desired, mixtures of gases may be used, for example, providing for the exceptions indicated hereinbefore, a mixture of carbon dioxide and nitrogen is advantageous in certain instances.

The invention is further illustrated with the following non-limiting examples.

EXAMPLE 1 preparation of catalyst compositions
Catalyst A

Lewatit M 500 WS (ex-Bayer, chloride form, exchange capacity 1.5 meq/ml), a strongly basic ion exchange resin of the quaternary ammonium type, was treated as follows in order to exchange the chloride anion ($Cl^-$) for bicarbonate ($HCO_3^-$):

- 150 ml (69.12 g) of wet resin was slurried in a water filled glass tube (60×2.5 cm)
- the resin was washed with 375 ml of methanol for 1 hr (LHSV: 2.5)
- the resin was dried with a stream of nitrogen for 1.5 hrs
- chloride was exchanged for bicarbonate by flushing the resin bed with an aqueous sodium bicarbonate solution (192 g of $NaHCO_3$ in 2500 g of water; 10 molar excess) for appr. 5 hrs (LHSV: 4)
- the exchanged resin was washed with 1200 ml of water for 2 h (LHSV: 4)

In this procedure 99.94% of the chloride anions were replaced by bicarbonate:

chloride content of untreated dried resin: 12.35 wt % chloride content of exchanged dried resin: 0.007 wt %.

Catalyst B

The chloride anion of the Lewatit M 500 WS was first exchanged for hydroxyl ($OH^-$) in a way as described for Catalyst A, by using as the flushing solution an aqueous sodium hydroxide solution (90 g of NaOH in 1500 g of water; 10 molar excess; 2.5 h and an LHSV of 4).

In this procedure 87% of the chloride anions were replaced by hydroxyl:

chloride content of untreated dried resin: 12.35 wt % chloride content of exchanged dried resin: 1.63 wt %.

The resulting resin in hydroxyl form was subsequently converted into the bicarbonate form by washing the resin with $CO_2$ saturated water and $CO_2$ gas (2 h; LHSV: 4) and washing with water (2 h; LHSV: 4).

Catalyst C

The chloride anion of the Lewatit M 500 WS was exchanged for bisulfate ($HSO_3^-$) in a way as described for Catalyst A, by using as the flushing solution an aqueous sodium bisulfate solution (234 g of $NaHSO_3$ in 1500 g of water; 10 molar excess; 2.5 h and an LHSV of 4).

In this procedure 99.98% of the chloride anions were replaced by bisulfate:

chloride content of untreated dried resin: 12.35 wt % chloride content of exchanged dried resin: 0.0028 wt %.

Catalyst D

The chloride anion of the Lewatit M 500 WS was exchanged for formate ($HCOO^-$) as described for Catalyst A, by using as the flushing solution an aqueous sodium formate solution (153 g of HCOONa in 1500 g of water; 10 molar excess).

In this procedure 99.97% of the chloride anions were replaced by formate:

chloride content of untreated dried resin: 12.35 wt % chloride content of exchanged dried resin: 0.004 wt %.

Catalyst E

Amberlite 400, (ex-Rohm & Haas, $Cl^-$ form, exchange capacity 1.4 meq/ml), a strongly basic anion exchange resin of the quaternary ammonium type, was charged with bicarbonate as follows:

- 40 ml (18.45 g) of wet resin was slurried in a water filled glass tube (60×2.5 cm)
- chloride was exchanged for bicarbonate by flushing the resin bed with an aqueous sodium bicarbonate solution (24 g of $NaHCO_3$ in 600 g of water)

Catalyst F

Duolite A 368 (ex-Duolite International Co.), a weakly basic anion exchange resin of the tertiary amine type, was treated by washing with $CO_2$-saturated water and $CO_2$ gas during 2.5 hrs (LHSV: 4), followed by pure water during 2 hrs (LHSV: 4).

In the following Examples 2–4, the solid components (Catalysts A-F and the unmodified Lewatit and Duolite resins) were used in wet, drained form and product samples were analyzed by gas chromatography to determine feed (EO and Propylene Oxide, respectively) conversion and selectivity to monoethylene glycol (MEG) and monopropylene glycol (MPG) respectively.

EXAMPLE 2 hydration of ethylene glycol in batch operation

A 550 ml autoclave was filled with the catalyst (35 g), water (90 g; 5 mol) and EO (44 g; 1 mol) and heated over 1 hour to 120° C. at 1100 pKa gas pressure. The gas added was pure nitrogen, pure carbon dioxide (resulting in 4.9 wt % $CO_2$ on water and EO intake in the autoclave) or a 2:98 $CO_2/N_2$ mixture (resulting in 0.1 wt % $CO_2$ on water and EO intake in the autoclave). The reaction mixture was maintained under continuous stirring for 2 hours at 120° C. The results are presented in Table 1.

TABLE 1

| | Batch conversion of EO | | | |
|---|---|---|---|---|
| Exp. No. | Solid Component | Gas cap | EO Conversion (% mol) | MEG Selectivity (% mol) |
| 2.1 | none | $N_2$ | 100 | 67.6 |
| 2.3 | Lewatit | $N_2$ | 99.9 | 53.4 |
| 2.3 | Lewatit | $N_2/CO_2$ | 100 | 76.4 |
| 2.4 | Cat A | $N_2$ | 99.7 | 89.7 |
| 2.5 | Cat A | $N_2/CO_2$ | 99.9 | 88.5 |
| 2.6 | Cat A | $CO_2$ | 99.9 | 81.2 |
| 2.7 | Cat B | $N_2$ | 99.9 | 92.7 |
| 2.8 | Cat B | $N_2/CO_2$ | 99.7 | 91.2 |
| 2.9 | Cat B | $CO_2$ | 100 | 79.9 |
| 2.10 | Cat C | N | 100 | 65.7 |
| 2.11 | Cat C | $CO_2$ | 100 | 70.4 |
| 2.12 | Cat D | $N_2$ | 99.9 | 84.8 |
| 2.13 | Cat D | $CO_2$ | 100 | 81.3 |
| 2.14 | Cat F | $N_2$ | 98.3 | 40.0 |
| 2.15 | Cat F | $CO_2$ | 99.9 | 82.1 |
| 2.16 | Doulite | $N_2$ | 99.8 | 37.8 |
| 2.17 | Doulite | $CO_2$ | 99.9 | 86.4 |

These data show that $CO_2$ was detrimental to the selectivity of the bicarbonate catalysts A and B and the formate catalyst D. By contrast, $CO_2$ was beneficial to the unmodified ion exchangers Lewatit and Duolite, for the bisulfite-on-Lewatit Catalyst C and for the $CO_2$ pre-treated Duolite Catalyst F.

EXAMPLE 3 hydration of ethylene glycol in continuous operation with Catalyst A 3.1, Effect of $CO_2$ added to the feed stream A water/EO feed (mol ratio 5:1) was pumped at 1600 kPa pressure with Liquid Hourly Space Velocity (LHSV) 2 over an isothermal (80° C.) fixed bed pipe reactor of 20 ml containing 20 ml of wet Catalyst A.

To study the effect of $CO_2$ in the feed the feed water was saturated with $CO_2$ and kept under a 400 kPa $CO_2$ pressure in the water feed vessel, resulting in 0.45 wt % of $CO_2$ in the feed water. Reactor outlet samples were taken periodically. The results are presented in Table 2.

TABLE 2

Continuous EO conversion; effect of $CO_2$ in the feed (Example 3.1)

| Run time (h) | Sample | $CO_2$ in feed | LHSV | EO Conversion (% mol) | MEG Selectivity (% mol) |
|---|---|---|---|---|---|
| 0 | 1 | no | 0.5 | 100 | 97 |
| 27 | 2 | yes | 0.5 | 74 | 93 |
| 30 | 3 | yes | 0.5 | 68 | 92 |
| 72 | 4 | yes | 1 | 45 | 95 |
| 96 | 5 | yes | 0.5 | 71 | 92 |
| 198 | 6 | no | 2 | 81 | 94 |
| 213 | 7 | no | 2 | 87 | 96 |
| 238 | 8 | no | 2 | 91 | 97 |
| 260 | 9 | no | 0.5 | 100 | 97 |
| 267 | 10 | no | 1 | 99 | 96 |

These results show that the presence of $CO_2$ in the feed is detrimental for the effect of Catalyst A on both EO conversion and selectivity to MEG. When the catalyst has been in contact with $CO_2$ containing feed, relatively long "regeneration" time is needed to return to original activity levels.

3.2, Stability test

The same experimental set-up was used with water, EO and Catalyst A as in Example 3.1, without $CO_2$ in the feed and during a total of 1820 hours. During that period process parameters were varied (LHSV between 1-10, mol ratio water: EO between 3-10, temperature between 60°-90° C.). The product stream was sampled periodically when the process conditions were "standard" as in Example 3.L (LHSV 2; mol ratio water:EO 5, temperature: 80° C.). The results are presented in Table 3.

TABLE 3

Continuous EO conversion; Stability test (Example 3.2)

| Run-time (h) | Sample | EO conversion (% mol) | MEG selectivity (% mol) |
|---|---|---|---|
| 330 | 1 | 98 | 97 |
| 352 | 2 | 98 | 98 |
| 906 | 3 | 97 | 97 |
| 1048 | 4 | 97 | 98 |
| 1711 | 5 | 96 | 97 |
| 1820 | 6 | 98 | 97 |

These results show that the catalyst did not deteriorate with regard to activity or selectivity during the long-run experiment.

EXAMPLE 4 hydration of propylene glycol in batch operation with Catalyst E

EXAMPLE 4.1

A 500 ml stainless steel autoclave was charged with 0.8 mole of propyleneoxide, 4.2 moles of water and 42 ml of Catalyst E was used.

The autoclave was pressurized with nitrogen (1100 kPa). The reaction temperature was 120° C. and the duration of 3.6 hours.

Analysis of the product showed that more than 99% of propyleneoxide had been converted and that the selectivity to monopropyleneglycol was 95.5% and for dipropyleneglycol 3.9%.

EXAMPLE 4.2

An experiment was carried out, substantially as described in Example 4.1, but whereby the amounts of propyleneoxide, water and catalyst composition were 0.4 mole, 2.1 mole and 40 ml, respectively and the reaction time was 2 hours.

Analysis of the product showed that more than 99% of propyleneoxide had been converted and that selectivity to monopropyleneglycol was 97.8% and for dipropyleneglycol 1.2%.

EXAMPLE 4.3

(for comparison)

An experiment was carried out similar to Example 4.1, but without catalyst and at a temperature of 160° C., the amounts of propyleneoxide and water being 1 mole and 5 moles, respectively and the reaction time 3 hours.

Analysis of the product showed that more than 99% of propyleneoxide had been converted and that selectivity to monopropyleneglycol was 81.5% and for dipropyleneglycol 17.8%.

What is claimed is:

1. A process for the preparation of alkylene glycols which comprises reacting an alkylene oxide with water in the presence of a catalyst composition comprising a solid material having one or more electropositive sites, which are coordinated with one or more anions other than metalate or halogen anions, with the proviso that when the solid material is an anionic exchange resin of the quaternary ammonium type and the anion is bicarbonate, the process is performed in the substantial absence of carbon dioxide.

2. The process as claimed in claim 1, characterized in that an alkylene oxide is chosen from the group of ethylene oxide and propylene oxide.

3. The process as claimed in claim 1, characterized in that the solid material is an anionic ion exchange resin.

4. The process as claimed in claim 3, characterized in that the anionic ion exchange resin is of the quaternary ammonium type.

5. The process as claimed in claim 1, characterized in that the anion is bisulfite.

6. The process as claimed in claim 1, characterized in that the anion is a carboxylate having from 1 to about 20 carbon atoms.

7. The process as claimed in claim 6, characterized in that the carboxylate is formate.

8. The process as claimed in claim 7, characterized in that said process is performed in the substantial absence of carbon dioxide.

9. The process as claimed in claim 1, characterized in that the anion is bicarbonate.

10. The process as claimed in claim 1, characterized in that the molar ratio between water and alkylene oxide is in the range of from about 1:1 to about 15:1, the reaction temperature is in the range of from about 80° C. to about 200° C., and the reaction pressure in the range of about 200 kPa to about 3000 kPa.

* * * * *